US010876146B2

(12) United States Patent
Pompa et al.

(10) Patent No.: US 10,876,146 B2
(45) Date of Patent: Dec. 29, 2020

(54) METHOD FOR THE COLORIMETRIC DETECTION OF CONTAMINATION WITH NUCLEASES (71) Applicant: Fondazione Istituto Italiano di Tecnologia, Genoa (IT)

(72) Inventors: Pier Paolo Pompa, Lecce (IT); Paola Valentini, Genoa (IT); Paola Cecere, Bari (IT)

(73) Assignee: Fondazione Istituto Italiano di Tecnología, Genoa (IT)

( * ) Notice: Subject to any disclaimer, the term of this patent is extended or adjusted under 35 U.S.C. 154(b) by 340 days.

(21) Appl. No.: 15/533,481

(22) PCT Filed: Dec. 11, 2015

(86) PCT No.: PCT/IB2015/059541
§ 371 (c)(1),
(2) Date: Jun. 6, 2017

(87) PCT Pub. No.: WO2016/097952
PCT Pub. Date: Jun. 23, 2016

(65) Prior Publication Data
US 2017/0335366 A1    Nov. 23, 2017

(30) Foreign Application Priority Data
Dec. 15, 2014  (IT) .............................. TO2014A1040

(51) Int. Cl.
*C12Q 1/34*    (2006.01)
*C12Q 1/68*    (2018.01)
*C12Q 1/6818*  (2018.01)

(52) U.S. Cl.
CPC ............. *C12Q 1/34* (2013.01); *C12Q 1/6818* (2013.01); *C12Q 2521/301* (2013.01);
(Continued)

(58) Field of Classification Search
CPC .......... C12Q 1/34; C12Q 1/68; C12Q 1/6181; C12Q 2521/301; C12Q 2521/307;
(Continued)

(56) References Cited

U.S. PATENT DOCUMENTS

2009/0155785 A1    6/2009    Mirkin et al.

FOREIGN PATENT DOCUMENTS

WO    2007/106118 A2    9/2007

OTHER PUBLICATIONS

Song et al., "A Simple, Universal Colorimetric Assay for Endonuclease/Methyltransferase Activity and Inhibition Based on an Enzyme-Responsive Nanoparticle System", ACS NANO, 2009, vol. 3, No. 5, pp. 1183-1189.
(Continued)

*Primary Examiner* — Terra C Gibbs
(74) *Attorney, Agent, or Firm* — MacMillan, Sobanski & Todd, LLC (57) ABSTRACT Method for detecting the presence of nucleases in a sample, characterized in that it comprises the steps of: —incubating the sample to be tested for the presence of nucleases with at least one oligonucleotide linker constituting the substrate for the nuclease to be detected, for a sufficient time to cause degradation of said oligonucleotide linker by the nuclease possibly present in the sample, —adding to the sample, upon incubation, colloidal gold nanoparticles comprising gold nanoparticles functionalized with a first probe oligonucleotide and gold nanoparticles functionalized with a respective second probe oligonucleotide, said first and second probe oligonucleotides being complementary to a respective portion of the nucleotide sequence of the oligonucleotide linker, and—examining the possible colour change of the sample as a result of the addition of said nanoparticles, a colour change of the sample to the colour assumed by the colloidal gold
(Continued)

particles when aggregated at a distance less than their size being indicative of the absence of the tested nuclease from the sample.

6 Claims, 1 Drawing Sheet

Specification includes a Sequence Listing.

(52) U.S. Cl.
CPC . *C12Q 2521/307* (2013.01); *C12Q 2521/319* (2013.01); *C12Q 2521/327* (2013.01); *C12Q 2563/137* (2013.01); *C12Q 2563/155* (2013.01); *C12Q 2565/113* (2013.01); *G01N 2333/916* (2013.01); *G01N 2333/922* (2013.01)

(58) Field of Classification Search
CPC ........ C12Q 2521/327; C12Q 2521/319; G01N 2333/922
See application file for complete search history.

(56) References Cited

OTHER PUBLICATIONS

Zhou et al., "DNA-responsive disassembly of AuNP aggregates: influence of nonbase-paired regions and colorimetric DNA detection by exonuclease III aided amplification", Journal of Materials Chemistry B, 2013, vol. 1, No. 22, pp. 2851-2858.

PCT International Search Report and the Written Opinion, Application No. PCT/IB2015/059541 filed Dec. 11, 2015, dated Apr. 6, 2016.

Cao et al., "Naked-eye sensitive detection of nuclease activity using positively-charged gold nanoparticles as colorimetric probes", Chemical Communications, 2011, vol. 47, pp. 12301-12303.

Giljohann et al., "Gene Regulation with Polyvalent siRNA—Nanoparticles Conjugates", Journal of the American Chemical Society, 2009, vol. 131, pp. 2072-2073.

Seferos et al., "Polyvalent DNA Nanoparticle Conjugates Stabilize Nucleic Acids", Nano Letters, 2009, vol. 9, No. 1, pp. 308-311.

Xu et al., "A Gold-Nanoparticle-Based Real-Time Colorimetric Screening Method for Endonuclease Activity and Inhibition", Angewandte Chemie International Edition, 2007, vol. 46, pp. 3468-3470.

METHOD FOR THE COLORIMETRIC DETECTION OF CONTAMINATION WITH NUCLEASES

This is a national stage application filed under 35 U.S.C. § 371 of international application PCT/IB2015/059541, filed under the authority of the Patent Cooperation Treaty on Dec. 11, 2015 published; which claims the benefit of Patent Application No. IT TO2014A001040 filed on Dec. 15, 2014. The entire disclosures of all the aforementioned applications are expressly incorporated herein by reference for all purposes.

The present invention relates to a method for detecting nucleases in a liquid sample in which the presence of nucleases is determined colorimetrically, utilizing the known property of colloidal gold nanoparticles (AuNPs) to give rise to a visible colour change when, as a result of their aggregation, the distance between the particles becomes less than the particle size (diameter).

The nucleases are ubiquitous and the number of enzymes characterized in this class is constantly increasing. They can be divided into exonucleases and endonucleases, depending on their capacity for digesting their substrate completely or incompletely. The nucleases are also divided into DNases and RNases, depending on whether, as the name suggests, they preferably degrade DNA or RNA, respectively.

A more detailed classification also considers the preference for structural characteristics of the substrate, distinguishing between enzymes specific for single-stranded or double-stranded nucleic acids, heteroduplex or nicked structures, mispaired DNA and others.

The ubiquitous character of the nucleases represents a problem for numerous applications that involve molecular biology experiments, in which contamination with nucleases is to be avoided.

Current solutions for preventing contamination with nucleases in ordinary laboratory practice include the use of sterile devices and instruments and the application of steps such as: thermal treatments at high temperature, treatment with diethyl pyrocarbonate (DEPC), which inactivates RNases, followed by autoclaving, addition of chelating agents, which increase the stability of RNA at high temperature in the presence of divalent cations.

Current solutions for detecting contamination with nucleases include the use of commercially available kits, mostly based on fluorescence reading or that require a gel electrophoresis step, which give a quite sensitive qualitative result, but have disadvantages that the present invention proposes to overcome.

Firstly, the commercial tests require suitable instrumentation for detection, such as a fluorometer or gel electrophoresis equipment, which is not necessary in the test according to the invention, which utilizes reading of a colour change that is visible to the naked eye. However, in tests based on fluorescence, the possibility of interpreting the results with the naked eye is based on positioning the test tube on a UV trans-illuminator, but this method gives lower sensitivity, which is also influenced by external conditions such as correct ambient illumination or the type of UV lamp used.

The commercial tests require a positive control based on a nuclease, which is itself a potential source of contamination, which may affect the test result and potentially compromise subsequent experiments. In contrast, the test according to the invention does not require the use of a positive control that uses a nuclease, as described hereunder.

In economic terms, the average cost of analysis for the commercial tests is relatively high (about €8 for the DNase test and up to about €30 for the RNase tests, taking into account three samples, including the test itself, the positive control and the negative control). One aim achieved by the invention is that it supplies a test of low cost.

The tests based on fluorescence have limitations for deeply coloured solutions. Regarding this point, the invention supplies a method with high sensitivity that makes it possible to perform the test on deeply coloured solutions. By diluting the coloured sample by up to 10 times, it is mostly possible to avoid interference with the deeply coloured colloid submitted to the test, losing only about an order of magnitude of sensitivity, which in the majority of cases is more than sufficient for evaluating even low levels of contamination. In particular, in one embodiment of the test, as illustrated hereunder, the sample is also added to the positive control test tube, so as to permit not only detection of the presence of potentially interfering components in the sample, but also removal of interference of lighter colour.

A further disadvantage of the majority of the commercial tests is due to the fact that they are designed for detecting specifically the activity of endonucleases; in contrast, the test according to the invention permits simultaneous detection of endonucleases and exonucleases.

Another disadvantage relates specifically to tests based on gel electrophoresis and staining of the reactions with SYBR gold. Since SYBR gold stains the nucleic acids, this methodology does not allow the test to be carried out on samples containing DNA or RNA, as staining of these nucleic acids interferes with the result. Since the test of the invention is based on the hybridization of complementary sequences, the presence of other nucleic acids (not complementary) does not interfere with the results, so that this extends the field of the various samples that can be analysed.

In the scientific literature there are some reports that utilize the optical properties of gold nanoparticles in various reaction schemes.

Cao et al. [ref 1] reported a test in which bare AuNPs, charged positively, are exposed to single-stranded DNA (ssDNA), which is adsorbed on their surface by electrostatic interactions and causes aggregation of them with consequent colour change from red to blue. In the presence of S1 nuclease, ssDNA is degraded and the AuNPs maintain the red coloration. The authors report a limit of detection of $4.3 \times 10^{-3}$ U/µl with a dynamic range below 7.

Xu et al. [ref. 2] describe a system based on functionalized AuNPs, which are crosslinked by means of an oligonucleotide linker. In the presence of DNAse I, the aggregate of AuNPs is digested by the enzyme and the AuNPs change colour from violet to red. The authors report a limit of detection of $1 \times 10^{-2}$ U/µl and illustrate implementation of the test on a dynamic range of 4, although they do not state explicitly that this is the final dynamic range of the method.

There are, however, appreciable differences between the test described there and the test according to the invention. In particular, in the test according to the invention, enzymatic digestion takes place in solution, so that it is much more efficient with respect to erosion of a large aggregate of AuNPs, because 1) in the test in the literature, degradation of the linker can only proceed starting from its externally exposed surface of the aggregate and 2) as is known, [ref 3] and [ref 4], the efficiency of nuclease enzymes is significantly reduced by interaction with AuNPs.

Moreover, the test proposed by Xu et al. only functions with DNaseI, whereas the test according to the invention is of a universal character. Moreover, in the test according to the invention, actuation of enzymatic digestion in solution offers the possibility of testing the activity both of exonucleases, and of endonucleases with the same system. This would not always be possible in the context of an aggregate of AuNPs as there would not be free ends of DNA accessible to the enzyme for initiating exonucleolytic scission.

To summarize, the invention has the aim of supplying a system that solves the aforementioned problems relating to the commercial tests and that offers better sensitivity and versatility relative to the tests proposed in the scientific literature.

In view of these aims, the invention relates to a method having the characteristics defined in the claims that follow, which constitute an integral part of the present invention.

The invention also relates to a kit for implementing the test.

In the method according to the invention, a small amount of the solution to be tested for the presence of nucleases (generally an amount of about 50 µl) is put in a test tube containing oligonucleotide linkers of DNA and/or RNA, generally lyophilized, which constitute the substrate for DNase or RNase, respectively. The sample is incubated for a sufficient time to cause degradation of the oligonucleotide linker by the nuclease possibly present in the sample. Typically, an incubation time of about one hour at room temperature may be sufficient (but shorter incubation times may be used in some specific cases). Alternatively, if higher sensitivity of the test is desired, incubation may be continued overnight. However, the sensitivity attained after one hour of incubation is already greater than the sensitivity of any other commercial test, so that prolonged incubation is only necessary for applications that require high sensitivity, i.e. when even trace contamination is undesirable.

During incubation, any nuclease or nucleases present cause degradation of the respective linker.

The amount of lyophilized linker present in the reaction tube is such that its final concentration in the test solution is rather low (from 10 nM to 1 µM, preferably from 50 nM to 500 nM), so as to maximize the sensitivity of the test.

The second and last step of the test consists of the addition of AuNP probes. Colloidal gold nanoparticles are used, typically capped with citrate, functionalized with oligonucleotides 1 and 2, designated hereinafter AuNP1 and AuNP2, where the oligonucleotide sequences 1 and 2 are complementary to a respective portion of the nucleotide sequence of the oligonucleotide linker.

In the presence of an intact substrate, as a result of the hybridization event, the AuNPs become crosslinked, leading to a visible colour change from red to purple/violet/blue. In contrast, in the presence of contamination of the specific class of nucleases that is being tested, the AuNPs do not undergo crosslinking, as a result of the degradation of linkers in the first step, and the solution still has the red coloration.

The test is universal as it uses universal AuNP probes and up to six different universal oligonucleotide linkers, which are substrates for the nucleases and cover all the commonest enzymatic specificities, including DNases specific for double strand and single strand, RNases specific for double and single strand, nucleases specific for heteroduplex DNA/RNA and exonucleases.

In the appended drawings.

Figure 1:
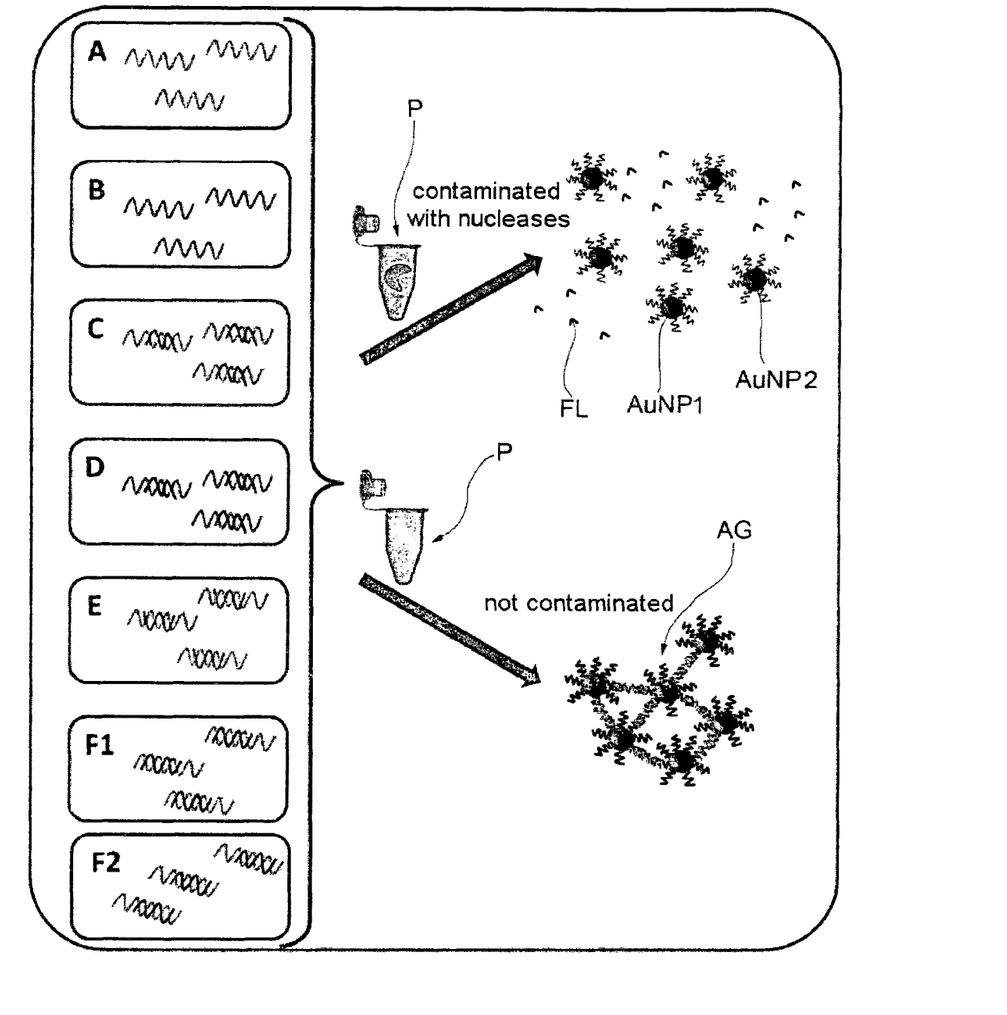
FIG. 1 shows a schematic representation of the test, where the letters A to F indicate different types of oligonucleotide linkers that can be used; AuNP1 and AuNP2 indicate the functionalized colloidal gold particles with the respective oligonucleotide, FL indicates the oligonucleotide linker fragments resulting from the enzymatic degradation, in the case when nucleases are present in the sample, AG indicates an aggregate of AuNP1 and AuNP2 resulting from hybridization, in the case of absence of nucleases, and P indicates the test tube containing the liquid sample submitted to the test.

A and B indicate oligonucleotide linkers consisting of sequences of ssDNA or ssRNA respectively, usable in the test for detecting DNase and RNase specific for single strand; these linkers cause aggregation of the functionalized AuNPs directly.

In general, the oligonucleotide linkers used as substrates are random sequences, devoid of significant secondary structure and not susceptible to dimerization. These sequences may optionally be modified chemically. Examples of oligonucleotide linkers of type A and B are as follows:

(A).

(SEQ ID NO: 1)
5' ATAAAGTGACAGAATAGAGTGA 3' (A1)
or:

(SEQ ID NO: 2)
5' AGTGACAGAATAGA 3' (A2)

(B).

(SEQ ID NO: 3)
5' ArUrArArArGrUrGrArCrArGrArArUrArGrArGrUr

GrA 3' (B1)
or:

(SEQ ID NO: 4)
5' ArGrUrGrArCrArGrArArUrArGrAr 3' (B2)
or:

(SEQ ID NO: 5)
5' ArGrUrGrArCrArUrCrCrGrArArUrArGrAr 3' (B3)
or:

(SEQ ID NO: 6)
5' rCrArUrUrGrCrUrUrCrArUrCrUrGrUrUrCrGr

UrCrU 3' (B4)
or:

(SEQ ID NO: 7)
5' rGrCrUrUrCrArUrCrUrGrUrUrUrC 3' (B5).

C, D and E indicate oligonucleotide linkers for detecting nucleases specific for dsDNA, dsRNA or heteroduplex DNA/RNA, respectively; in these oligonucleotide linkers, the same linker sequence A or B is hybridized to a shorter complementary oligonucleotide sequence, consisting of DNA or RNA, so that the hybrids have at least one single-stranded free end, designed so that a strand displacement occurs as a result of binding with functionalized AuNPs.

Examples of oligonucleotide linkers of type C, D and E are as follows:
(C) dsDNA sequence consisting of (A1) and 5' TCT ATT CTG TCA CT 3' (SEQ ID NO:8)
(D) dsRNA sequence consisting of (B1) and 5' rUrCrUrA-rUrUrCrUrGrUrCrArCrU 3' (SEQ ID NO:9)
(E) DNA/RNA heteroduplex consisting of (A1) and 5' rUrCrUrArUrUrCrUrGrUrCrArCrU 3' (SEQ ID NO:9) or DNA/RNA heteroduplex consisting of (B1) and 5' TCT ATT CTG TCA CT 3' (SEQ ID NO:8).

Finally, in the case of exonucleases, the oligonucleotide linker, indicated with F1 or F2 as described hereunder, is incorporated into a dsDNA with one of the 2 blunt ends or with an overhang of not more than 4 bases.

Various types of exonucleases can digest double-stranded DNA (dsDNA) with blunt ends starting from the 5' or 3' end.

Depending on the type of exonuclease to be detected, 2 different substrates may be used, F1 and F2.

Examples of oligonucleotide linkers of type F1 and F2 are as follows:
(F1) dsDNA consisting of the aforementioned sequence (A) and 5' TATTCTGTCACTTTAT 3' (SEQ ID NO:10).
(F1bis) dsDNA consisting of 5'ATA AAG TGA CAG AAT A GAG TGA CAT 3' (SEQ ID NO:11) and 5' ATGTCACTCTAT 3' (SEQ ID NO:12).

These substrates are digested starting from the blunt end 5' by all the exonucleases with specificity of type 5'→3'.

The overhang 3', in the absence of enzymatic digestion, will cause aggregation of the AuNPs by strand displacement.
(F2) dsDNA consisting of the aforementioned sequence (A) and 5' TCACTCTATTCTGTC 3' (SEQ ID NO:13).
(F2bis) dsDNA consisting of 5' CGTATAAAGTGACAGAATAGAGTGA 3' (SEQ ID NO:14) and 5' GCTTATTTCACT 3' (SEQ ID NO:15).

These substrates are digested starting from the blunt end 3' by all the exonucleases with specificity of type 3'→5'.

The overhang 5', in the absence of enzymatic digestion, will cause aggregation of the AuNPs by strand displacement.

As already stated, the probe oligonucleotides with which the colloidal gold particles are functionalized have a sequence complementary to at least one respective portion of the nucleotide sequence of the oligonucleotide linker used; in a preferred embodiment, the probe oligonucleotides 1 and 2 are each complementary to half of the sequence of the oligonucleotide linker.

However, the minimum number of nucleotides necessary for hybridization is equal to 4 or 5. It is possible that the portion of oligonucleotide probe that hybridizes to the linker is shorter than half of the linker. In the examples of linkers given above, this case is also envisaged. In every case, the total length of the probe oligonucleotide is preferably greater than half of the linker, unless the oligonucleotide linker is particularly long, as the gold nanoparticle is more stable if functionalized with probes of a certain length.

Typically, the probe oligonucleotides have a length of from 5 to 80 nucleotides, preferably of from 15 to 40 nucleotides.

The probe oligonucleotides may be chemically modified by binding with the gold nanoparticles; they may have spacer sequences for optimizing the efficiency of the reactions. Examples of oligonucleotide probes are as follows:

```
1.
                                        (SEQ ID NO: 16)
5' ATGTCACTCTATTC 3'
or:

(SEQ ID NO: 17)
5' ATGAGACGAAACAG 3'

2.
                                        (SEQ ID NO: 18)
5' TGTCACTTTATACG 3'
or:

(SEQ ID NO: 19)
5' ATGAAGCAATGACG 3'.
```

The functionalization density is typically between $2\times10^{-4}/nm^2$ and $2\times10^{-1}/nm^2$, preferably between $1\times10^{-3}/nm^2$ and $8\times10^{-2}/nm^2$.

The colloidal gold particles used typically have a size from 1 to 500 nm, preferably between 15 and 80 nm.

A kit for carrying out the method may comprise:
an aliquot of colloidal gold particles, preferably with citrate protection, sufficient for carrying out one or more tests,
probe oligonucleotides of type 1 and 2 mentioned above, or alternatively
colloidal gold particles already functionalized with said probe oligonucleotides 1 and 2, and
one or more oligonucleotide linkers of the aforementioned type preferably in lyophilized form. Preferably, the kit comprises oligonucleotide linkers in the six forms mentioned above.

Depending on the type of contamination with nucleases that the user wishes to check, the user can decide whether to use all the substrates in parallel or only a portion thereof. The reaction will, however, be substantially identical for all the tests, including: addition of the sample to the appropriate test tube containing the respective oligonucleotide linker and optionally to control test tubes, incubation (for example for one hour or for shorter or longer times as mentioned above) and addition of the functionalized colloidal gold particles with the probe oligonucleotides of type 1 and 2 and visual determination of any colour change.

The method may comprise the carrying out of a negative control, carried out using only functionalized gold particles and the respective oligonucleotide linker, but in the absence of the sample to be analysed, replaced with an equivalent quantity of water without nucleases; the negative control gives rise to a purple/violet or blue coloration of the solution due to aggregation of the AuNPs. If the solution of the sample tested turns purple/violet/blue, like the negative control, this signifies that the sample is free from contamination with the nuclease that is to be detected.

Carrying out of the method may comprise the carrying out of a positive control test, using a solution containing only the functionalized colloidal gold particles and the sample to be tested, but without using the respective oligonucleotide linker.

In carrying out the positive control, the solution will maintain its red coloration, or in the case of interference with the components of the sample to be tested, will provide an indication that in the specific case the test cannot be performed; this may occur, for example, if we wish to perform detection on a concentrated and/or strongly coloured solution. In this way the positive control test does not require addition of a nuclease, as is required in the majority of commercial tests, and this makes the test according to the invention more reliable as it avoids the test itself being a potential source of contamination with nucleases in the laboratory or in the working environment.

The limit of detection tested in the tests carried out in the test according to the invention is $8\times10^{-5}$ U/μl or $2\times10^{-3}$ units in the total reaction volume, for the reaction applied for testing DNase I. For RNase A, the sensitivity is even higher as it reaches values of $1.75\times10^{-7}$ U per reaction. Moreover, the test has a high value of dynamic range equal to 1000 for DNase I (from 2 U to $2\times10^{-3}$ U) and 100 000 000 (from 17.5 U to $1.75\times10^{-7}$) for RNase A.

Example 1: Detection of DNase

An aliquot of the test solution equal to 50 μl is added to a reaction tube containing a small amount of lyophilized substrate (A1) or (C), or to both. The final concentration of the substrate in the solution is 100 nM. Various reaction tubes are prepared, containing variable amounts of the enzyme DNase I (from 200 units to $2\times10^{-4}$ units). The solution is left to incubate for one hour, or less in specific cases, at room temperature. An identical amount (50 µl) of water free from nucleases is added to a second identical reaction tube (negative control) containing the same substrate. A third tube (positive control) is instead empty. An identical aliquot of the test solution is added to this. At the end of incubation, a mix of colloidal gold nanoparticles (AuNPs) is added to all the tubes, for a concentration of 1 nM in the final solution. This mix contains, in equal proportions, AuNPs functionalized with two different probe sequences of DNA, probe oligonucleotide 1, with the sequence 5' ATGTCACTCTATTC 3' (SEQ ID NO:12), and probe oligonucleotide 2, with the sequence 5' TGTCACTT-TATACG 3' (SEQ ID NO:14). After brief incubation, the possible colour change is observed, indicative of the absence of contamination. In the negative control the colour change is observed in every case. In the positive control, colour change is not observed, unless substances that interfere with the colorimetric test are present in the solution. In this case, this control offers the possibility of removing small interferences visually, or of deciding the possible non-testability of the sample, if the interference is excessive. This sample containing interfering components may, however, be suitably diluted and tested again. In the samples containing DNase I, the colour change is not observed for the samples that contain from 200 units to $2 \times 10^{-3}$ units of DNase I. $2 \times 10^{-3}$ units thus represents the limit of detection of the test for DNase I.

Example 2: Detection of RNase

An aliquot of the test solution equal to 50 µl is added to a reaction tube containing a small amount of lyophilized substrate (B1) or (D). The final concentration of the substrate in the solution is 75 nM. Various reaction tubes are prepared, containing variable amounts of the enzyme RNase, A (from 1.75 units to $1.75 \times 10^{-7}$ units). The solution is left to incubate for one hour, or less in specific cases, at room temperature. An identical amount (50 µl) of water free from nucleases is added to a second identical reaction tube (negative control) containing the same substrate. A third tube (positive control) is instead empty. An identical aliquot of the test solution is added to this. At the end of incubation, a mix of colloidal gold nanoparticles (AuNPs) is added to all the tubes, for a concentration of 1 nM in the final solution. This mix contains, in equal proportions, AuNPs functionalized with two different probe sequences of DNA, probe oligonucleotide 1, with the sequence 5' ATGTCACTCT-ATTC 3' (SEQ ID NO:12), and probe oligonucleotide 2, with the sequence 5' TGTCACTTTATACG 3' (SEQ ID NO:14). After brief incubation, the possible colour change is observed, indicative of the absence of contamination, as described in example 1. In the samples containing RNase A, the colour change is not observed for the samples that contain from 1.75 units to $1.75 \times 10^{-7}$ units of RNase A. $1.75 \times 10^{-7}$ units thus represents the limit of detection of the test for RNase A.

The method according to the invention was validated using various nucleases, including DNase I, RNase A, Mung Bean nuclease, micrococcal nuclease, nucleases Bal-31, RNase H and extracellular bacterial DNases. The method proved to be capable of detecting all the enzymes tested that display varied substrate specificity. As already mentioned, the method was optimized for six different substrates, thus allowing six classes of enzymes to be tested, including the enzymes mentioned above. However, the test is intended to be extendable to other nucleases, using the same test principle.

The test can therefore be applied widely in all situations where accurate and rapid inspection for the presence of any contamination with nucleases is required, for example in quality control tests in laboratory practice and thus also in quality control of reagents for molecular biology and of laboratory plasticware, as well as in scientific research applications.

Furthermore, the test provides information on the specific type of contamination present in the sample, allow specific strategies for inactivation to be defined, which may be more suitable than generalized procedures for nuclease decontamination.

REFERENCES

Rui Cao, Baoxin Li, Yuanfu Zhang and Zhining Zhang, Naked-eye sensitive detection of nuclease activity using positively-charged gold nanoparticles as colorimetric probes, Chem. Commun., 2011, 47, 12301-12303

Xiaoyang Xu, Min Su Han, and Chad A. Mirkin, A Gold-Nanoparticle-Based Real-Time Colorimetric Screening Method for Endonuclease Activity and Inhibition, Angew. Chem. Int. Ed., 2007, 46, 3468-3470

David A. Giljohann, Dwight S. Seferos, Andrew E. Prigodich, Pinal C. Patel, and Chad A. Mirkin, Gene Regulation with Polyvalent siRNA-Nanoparticle Conjugates, J. Am. Chem. Soc., 2009, 131, 2072-2073

Dwight S. Seferos, Andrew E. Prigodich, David A. Giljohann, Pinal C. Patel, and Chad A. Mirkin, Polyvalent DNA Nanoparticle Conjugates Stabilize Nucleic Acids, Nano Lett., 2009, 9, 308-311.

The invention claimed is:

1. A method for detecting DNase or RNase specific for single-stranded DNA or RNA, respectively, characterized in that the method comprises the steps of:

incubating a sample to be tested for the presence of nucleases with at least one oligonucleotide linker constituting a substrate for the nuclease to be detected, for a time sufficient to cause degradation of said oligonucleotide linker by the nuclease present in the sample, adding to the sample, upon incubation, colloidal gold nanoparticles comprising gold nanoparticles functionalized with a first probe oligonucleotide and gold nanoparticles functionalized with a respective second probe oligonucleotide, said first and second probe oligonucleotide being complementary to a respective portion of the nucleotide sequence of the oligonucleotide linker, and examining the color shift of the sample as a result of the addition of said nanoparticles, a color shift of the sample to the color assumed by the colloidal gold particles when aggregated at a distance less than their size being indicative of the absence of the tested nuclease from the sample;

in which the oligonucleotide linker is a single-stranded DNA or RNA sequence devoid of secondary structure and not dimerizing, characterized in that the oligonucleotide linker is selected from the group consisting of:

(SEQ ID NO: 1)
5' ATAAAGTGACAGAATAGAGTGA 3';

(SEQ ID NO: 2)
5' AGTGACAGAATAGA 3';

(SEQ ID NO: 3)
5' ArUrArArArGrUrGrArCrArGrArArUrArGrArGrUr GrA 3';

-continued

```
                                          (SEQ ID NO: 4)
5' ArGrUrGrArCrArGrArArUrArGrAr 3';
                                          (SEQ ID NO: 5)
5' ArGrUrGrArCrArUrCrCrGrArArUrArGrAr 3';
or:
                                          (SEQ ID NO: 6)
5' rCrArUrUrGrCrUrUrCrArUrCrUrGrUrUrCrGrUr

CrU 3';
and,
                                          (SEQ ID NO: 7)
5'rGrCrUrUrCrArUrCrUrGrUrUrC 3'.
```

2. A method for detecting a nuclease specific for dsDNA, dsRNA and/or heteroduplex DNA/RNA,
characterized in that the method comprises the steps of:
incubating a sample to be tested for the presence of nucleases with at least one oligonucleotide linker constituting a substrate for the nuclease to be detected, for a time sufficient to cause degradation of said oligonucleotide linker by the nuclease present in the sample,
adding to the sample, upon incubation, colloidal gold nanoparticles comprising gold nanoparticles functionalized with a first probe oligonucleotide and gold nanoparticles functionalized with a respective second probe oligonucleotide, said first and second probe oligonucleotide being complementary to a respective portion of the nucleotide sequence of the oligonucleotide linker, and
examining the color shift of the sample as a result of the addition of said nanoparticles, a color shift of the sample to the color assumed by the colloidal gold particles when aggregated at a distance less than their size being indicative of the absence of the tested nuclease from the sample;
wherein the oligonucleotide linker comprises a DNA or RNA sequence, respectively, hybridized to a shorter complementary sequence to form a hybrid sequence having at least one single-stranded free end,
wherein said shorter complementary sequence is capable of strand displacement as a result of the hybridization of the single-stranded end with a complementary portion of the probe oligonucleotide that functionalizes the nanoparticles;
characterized in that said oligonucleotide linker is selected from the group consisting of:
a dsDNA sequence consisting of SEQ ID NO:1 and hybridized to a
dsDNA sequence consisting of 5'TCTATTCTGTCACT 3' (SEQ ID NO:8);
a dsRNA sequence consisting of SEQ ID NO:3 and hybridized to a
dsRNA sequence consisting of 5'rUrCrUrArUrUrCrUrGrUrCrArCrU 3' (SEQ ID NO:9);
a DNA/RNA heteroduplex consisting of SEQ ID NO:1 and hybridized to a
DNA/RNA heteroduplex consisting of 5'rUrCrUrArUrUrCrUrGrUrCrArCrU 3' (SEQ ID NO:9); or
a DNA/RNA heteroduplex consisting of SEQ ID NO:3 and hybridized to a
DNA/RNA heteroduplex consisting of 5'TCTATTCTGTCACT 3' (SEQ ID NO:8).

3. A method for detecting an exonuclease, characterized in that the method comprises the steps of:
incubating a sample to be tested for the presence of nucleases with at least one oligonucleotide linker constituting a substrate for the nuclease to be detected, for a time sufficient to cause degradation of said oligonucleotide linker by the nuclease present in the sample,
adding to the sample, upon incubation, colloidal gold nanoparticles comprising gold nanoparticles functionalized with a first probe oligonucleotide and gold nanoparticles functionalized with a respective second probe oligonucleotide, said first and second probe oligonucleotide being complementary to a respective portion of the nucleotide sequence of the oligonucleotide linker, and
examining the color shift of the sample as a result of the addition of said nanoparticles, a color shift of the sample to the color assumed by the colloidal gold particles when aggregated at a distance less than their size being indicative of the absence of the tested nuclease from the sample;
wherein the oligonucleotide linker is incorporated into a dsDNA sequence having a blunt end or an overhang of not more than 4 bases,
wherein the oligonucleotide linker is a dsDNA sequence having a blunt end consisting of:
SEQ ID NO:1 and 5'TATTCTGTCACTTTAT 3' (SEQ ID NO:10), or
SEQ ID NO:1 and 5'TCACTCTATTCTGTC 3' (SEQ ID NO:13), or
5'ATAAAGTGATGACATGAGCAGAATA 3' (SEQ ID NO:11) and 5' ATGTCACTCTAT 3' (SEQ ID NO:12), or 5'CGTATAAAGTGACAGAATAGAGTGA 3' (SEQ ID NO:14) and 5'GCTTATTTCACT 3' (SEQ ID NO:15).

4. A method for detecting the presence of nucleases in a sample, characterized in that the method comprises the steps of:
incubating a sample to be tested for the presence of nucleases with at least one oligonucleotide linker constituting a substrate for the nuclease to be detected, for a time sufficient to cause degradation of said oligonucleotide linker by the nuclease present in the sample,
adding to the sample, upon incubation, colloidal gold nanoparticles comprising gold nanoparticles functionalized with a first probe oligonucleotide and gold nanoparticles functionalized with a respective second probe oligonucleotide, said first and second probe oligonucleotide being complementary to a respective portion of the nucleotide sequence of the oligonucleotide linker, and
examining the color shift of the sample as a result of the addition of said nanoparticles, a color shift of the sample to the color assumed by the colloidal gold particles when aggregated at a distance less than their size being indicative of the absence of the tested nuclease from the sample,
characterized in that said first and second probe oligonucleotides have a length of from 5 to 80 nucleotides, or of from 15 to 40 nucleotides,
characterized in that said first probe oligonucleotide is selected from the group consisting of:
5'ATGTCACTCTATTC 3' (SEQ ID NO:16) and 5'ATGAGACGAAACAG 3' (SEQ ID NO:17) and further characterized in that said second probe oligonucleotide is selected from the group consisting of 5'TGTCACTTTATACG 3' (SEQ ID NO:18) and 5'ATGAAGCAATGACG 3' (SEQ ID NO:19).

5. A method for detecting the presence of nucleases in a sample, characterized in that the method comprises the steps of:

incubating the sample to be tested for the presence of nucleases with at least one oligonucleotide linker constituting a substrate for the nuclease to be detected, for a time sufficient to cause degradation of said oligonucleotide linker by the nuclease present in the sample, adding to the sample, upon incubation, colloidal gold nanoparticles comprising gold nanoparticles functionalized with a first probe oligonucleotide and gold nanoparticles functionalized with a respective second probe oligonucleotide, said first and second probe oligonucleotide being complementary to a respective portion of the nucleotide sequence of the oligonucleotide linker, and examining the color shift of the sample as a result of the addition of said nanoparticles, a color shift of the sample to the color assumed by the colloidal gold particles when aggregated at a distance less than their size being indicative of the absence of the tested nuclease from the sample, wherein said colloidal gold nanoparticles are functionalized with said probe oligonucleotides at a functionalization density of from $2\times10^{-4}/nm^2$ to $2\times10^{-1}/nm^2$.

6. The method according to claim 5, wherein said colloidal gold nanoparticles are functionalized with said probe oligonucleotides at a functionalization density of from $1\times10^{-3}/nm^2$ to $8\times10^{-2}/nm^2$.

* * * * *

SEQUENCE LISTING

```
<160> NUMBER OF SEQ ID NOS: 19

<210> SEQ ID NO 1
<211> LENGTH: 22
<212> TYPE: DNA
<213> ORGANISM: artificial
<220> FEATURE:
<223> OTHER INFORMATION: Oligonucleotide linker

<400> SEQUENCE: 1
ataaagtgac agaatagagt ga                                          22

<210> SEQ ID NO 2
<211> LENGTH: 14
```

```
<212> TYPE: DNA
<213> ORGANISM: artificial
<220> FEATURE:
<223> OTHER INFORMATION: Oligonucleotide linker

<400> SEQUENCE: 2
agtgacagaa taga                                                           14

<210> SEQ ID NO 3
<211> LENGTH: 22
<212> TYPE: RNA
<213> ORGANISM: artificial
<220> FEATURE:
<223> OTHER INFORMATION: Oligonucleotide linker

<400> SEQUENCE: 3
auaaagugac agaauagagu ga                                                  22

<210> SEQ ID NO 4
<211> LENGTH: 14
<212> TYPE: RNA
<213> ORGANISM: artificial
<220> FEATURE:
<223> OTHER INFORMATION: Oligonucleotide linker

<400> SEQUENCE: 4
agugacagaa uaga                                                           14

<210> SEQ ID NO 5
<211> LENGTH: 17
<212> TYPE: RNA
<213> ORGANISM: artificial
<220> FEATURE:
<223> OTHER INFORMATION: Oligonucleotide linker

<400> SEQUENCE: 5
agugacaucc gaauaga                                                        17

<210> SEQ ID NO 6
<211> LENGTH: 22
<212> TYPE: RNA
<213> ORGANISM: artificial
<220> FEATURE:
<223> OTHER INFORMATION: Oligonucleotide linker

<400> SEQUENCE: 6
cauugcuuca ucuguuucgu cu                                                  22

<210> SEQ ID NO 7
<211> LENGTH: 14
<212> TYPE: RNA
<213> ORGANISM: artificial
<220> FEATURE:
<223> OTHER INFORMATION: Oligonucleotide linker

<400> SEQUENCE: 7
gcuucaucug uuuc                                                           14

<210> SEQ ID NO 8
<211> LENGTH: 14
<212> TYPE: DNA
<213> ORGANISM: artificial
<220> FEATURE:
<223> OTHER INFORMATION: Oligonucleotide linker fragment

<400> SEQUENCE: 8
```
tctattctgt cact                                                 14

<210> SEQ ID NO 9
<211> LENGTH: 14
<212> TYPE: RNA
<213> ORGANISM: artificial
<220> FEATURE:
<223> OTHER INFORMATION: Oligonucleotide linker fragment

<400> SEQUENCE: 9
ucuauucugu cacu                                                 14

<210> SEQ ID NO 10
<211> LENGTH: 16
<212> TYPE: DNA
<213> ORGANISM: artificial
<220> FEATURE:
<223> OTHER INFORMATION: Oligonucleotide linker fragment

<400> SEQUENCE: 10
tattctgtca ctttat                                               16

<210> SEQ ID NO 11
<211> LENGTH: 25
<212> TYPE: DNA
<213> ORGANISM: artificial
<220> FEATURE:
<223> OTHER INFORMATION: Oligonucleotide linker fragment

<400> SEQUENCE: 11
ataaagtgac agaatagagt gacat                                     25

<210> SEQ ID NO 12
<211> LENGTH: 12
<212> TYPE: DNA
<213> ORGANISM: artificial
<220> FEATURE:
<223> OTHER INFORMATION: Oligonucleotide linker fragment

<400> SEQUENCE: 12
atgtcactct at                                                   12

<210> SEQ ID NO 13
<211> LENGTH: 15
<212> TYPE: DNA
<213> ORGANISM: artificial
<220> FEATURE:
<223> OTHER INFORMATION: Oligonucleotide linker fragment

<400> SEQUENCE: 13
tcactctatt ctgtc                                                15

<210> SEQ ID NO 14
<211> LENGTH: 25
<212> TYPE: DNA
<213> ORGANISM: artificial
<220> FEATURE:
<223> OTHER INFORMATION: Oligonucleotide linker fragment

<400> SEQUENCE: 14
cgtataaagt gacagaatag agtga                                     25

<210> SEQ ID NO 15
<211> LENGTH: 12
<212> TYPE: DNA
<213> ORGANISM: artificial

```
<220> FEATURE:
<223> OTHER INFORMATION: Oligonucleotide linker fragment

<400> SEQUENCE: 15
gcttatttca ct                                                          12

<210> SEQ ID NO 16
<211> LENGTH: 14
<212> TYPE: DNA
<213> ORGANISM: artificial
<220> FEATURE:
<223> OTHER INFORMATION: Oligonucleotide probe

<400> SEQUENCE: 16
atgtcactct attc                                                        14

<210> SEQ ID NO 17
<211> LENGTH: 14
<212> TYPE: DNA
<213> ORGANISM: artificial
<220> FEATURE:
<223> OTHER INFORMATION: Oligonucleotide probe

<400> SEQUENCE: 17
atgagacgaa acag                                                        14

<210> SEQ ID NO 18
<211> LENGTH: 14
<212> TYPE: DNA
<213> ORGANISM: artificial
<220> FEATURE:
<223> OTHER INFORMATION: Oligonucleotide probe

<400> SEQUENCE: 18
tgtcacttta tacg                                                        14

<210> SEQ ID NO 19
<211> LENGTH: 14
<212> TYPE: DNA
<213> ORGANISM: artificial
<220> FEATURE:
<223> OTHER INFORMATION: Oligonucleotide probe

<400> SEQUENCE: 19
atgaagcaat gacg                                                        14
```